United States Patent
Primbsch

[11] 4,132,117
[45] Jan. 2, 1979

[54] ULTRASONIC ENERGY RECEIVER PROBE UTILIZING OPTO-ELECTRICAL SENSING

[75] Inventor: Erik Primbsch, Cologne, Fed. Rep. of Germany

[73] Assignee: Krautkramer-Branson, Incorporated, Stratford, Conn.

[21] Appl. No.: 802,320

[22] Filed: Jun. 1, 1977

[30] Foreign Application Priority Data

Oct. 18, 1976 [DE] Fed. Rep. of Germany ....... 2646972

[51] Int. Cl.² ........................................... G01N 29/04
[52] U.S. Cl. ......................................... 73/607; 73/655
[58] Field of Search ................ 73/600, 605, 606, 607, 73/608, 618, 620, 624, 627, 632, 647, 655, 657; 340/5 H, 5 MP

[56] References Cited
U.S. PATENT DOCUMENTS
4,012,951  3/1977  Kessler .................................. 73/606

FOREIGN PATENT DOCUMENTS
1239124  7/1971  United Kingdom ................. 73/67.5 H

OTHER PUBLICATIONS
G. Alers et al., Visualization of Surface Elastic Waves on Structural Materials, Ultrasonics, Jul., 1973, pp. 174–177.

R. Mezrich et al., Ultrasonic Waves: Their Interferometric Measurement and Display, Applied Optics, Jun., 1976, pp. 1499–1505.

*Primary Examiner*—Richard C. Queisser
*Assistant Examiner*—John P. Beauchamp
*Attorney, Agent, or Firm*—Ervin B. Steinberg; Philip J. Feig

[57] ABSTRACT

A receiver probe for ultrasonic energy is described in which the surface deformation caused by compressive wave energy affects a thin gas-filled gap, its width being in the order of $10^{-7}$ meter. The gap is formed by opposing surfaces of an optical prism and an optical interference means. A beam of light is conducted to the boundary surface between the prism and gas. Changes in reflected and/or transmitted light beam portions resulting from compressive wave energy induced changes in gap width are sensed by opto-electric means.

23 Claims, 8 Drawing Figures

ULTRASONIC ENERGY RECEIVER PROBE UTILIZING OPTO-ELECTRICAL SENSING

GENERAL BACKGROUND

This invention concerns an apparatus for nondestructive testing of workpieces by ultrasonic energy and for measuring acoustic fields in liquid or solid materials which convert ultrasonic signals to optical signals and which latter signals are then transferred by opto-electrical devices, for instance photoelectric diodes, to electric signals.

When testing workpieces with ultrasonic pulse signals, particularly with shock wave energy, receivers are needed which operate free of resonance over a large bandwidth. It is desired that the receivers transform the ultrasonic wave amplitude, particularly the ultrasonic pressure amplitude, in a linear manner to amplitude proportional electrical signals.

For a true representation of the ultrasonic field it should be possible to achieve a useable localized resolution of the sound beam cross section.

Receiver transducers are known which operate either on the principle of a mechanical-electrical transducer (piezoelectric, magnetostrictive or similar transducer) or which utilize acoustic-optical effects.

In the case of mechanical-electrical transducers, mechanical structures are involved capable of vibrating at predetermined resonance conditions. Within the range of the resonant frequency, the pulse signal is greatly distorted and a linear transformation of very short ultrasonic pulse signals to electricl signals is not possible on account of the continuing ringing of the transducer. In order to avoid these disadvantages the transducers are severely damped by electrical or mechanical means or, alternatively, they are driven far outside their resonant freqeuncy. These measures lead to a considerable loss of sensitivity when mechanical to electrical signal transformation is utilized.

Optical methods are more advantageous inasmuch as the light beam is weightless and resonant frequencies cannot be produced when optical receiving means are used. Such methods differ as a result of the geometric configuration of the receiving mode:

1. The beam spread direction of the light and of the sound subtends a larger angle, e.g. Schlieren optics. In this case a localized resolution of the acoustic field is impossible. The acoustic field value is measured integrated over the light beam volume.
2. Methods in which the beam spread direction of the sound and of the light is colinear, e.g. optical interference arrangement. In this case, the deflection of a surface resulting from ultrasonic energy is measured, see U.S. patent application Ser. No. 629,062 of W. Kaule filed Nov. 5, 1975, now U.S. Pat. No. 4,046,477 dated Sept. 6, 1977. This method makes it possible to obtain localized resolution, that is, for each point in space of the acoustic field there is a signal amplitude which is proportional to the acoustic field amplitude whereby the degree of proportionality, i.e. the linearity of transformation, is very good. The disadvantage of these methods resides in the fact that monochromatic light must be used and that the apparatus must be constructed to be insensitive to mechanical shocks and temperature changes.

SUMMARY OF THE INVENTION

The present invention has as its purpose to provide a receiving system which is free of inertia and, therefore, is free of any resonance, thus enabling very short sonic energy pulses to be transformed by transducing means into electrical signals without pulse distortion, that is distortion-free. Furthermore, the present invention avoids integration over larger spatial elements and provides, therefore, good resolutions of the acoustic field by means of electrical signal representation.

The problem presented is solved by an arrangement which utilizes the known effects resulting from disturbed total reflection, also termed "frustrated" total reflection. In the case of total reflection, a portion of the light enters the optically thinner medium. This portion is very small and is reduced rapidly as a function of depth penetration in the optically thinner medium. As described in "Einfuehrung in die theoretische Physik" (book), Clemens Schaefer, Volume 3, Part 1, pages 413–420, Berlin (Germany) 1932; "Untersuchungen ueber die Totalreflexion", Clemens Schaefer et al., Annalen der Physik, 4th Sect., Vol. 32 (1910), pp 648–672; and article by W. Kaule et al., Messen and Pruefen (magazine), July/August 1974, pp 427–433, light incident upon the interface between two transparent media having refraction indexed $n_1$ and $n_2$ (for instance glass and air) is divided into a reflected and a refracted portion. If the angle of incidence $\alpha$ in the optically denser medium is greater than a limiting angle $\alpha_{limit}$ total reflection occurs, that is all of the incident light is reflected. The condition $\sin \alpha_{limit} = n_2/n_1$ applies. Despite the fact that the total reflection is free of losses, a light wave nonetheless will be apparent in the optically thinner medium. The amplitude of this light wave decreases exponentially as a function of the distance from the interface surface between the two media and decays already in about one wavelength. If a second and denser medium (e.g. glass) is placed in such close proximity to the interface surface that the light wave present in the thinner medium enters now the feeding denser medium, total reflection is disturbed or interfered with. Based on mathematical analysis it can be shown that the phenomenon of disturbed total reflection is limited to gap widths which are less than about one wavelength of light.

If air disposed in the gap between the two described media (glass) is subjected to an acoustic wave which, for example, is incident along a perpendicular axis upon one of the gap abutting surfaces, the gap thickness changes at the frequency of the acoustic wave. This causes a 180 degrees out of phase intensity modulation of the transmitted and of the reflected light portion. A narrowing of the gap causes a reduction of the intensity of the reflected light and an increase of the transmitted light portion. Conversely, an increase of the gap distance causes the opposite effect. Therefore, by monitoring the transmitted light or reflected light, using appropriate photoelectric means, the presence or absence as well as changes of an acoustic wave can be detected.

Based on the foregoing description, the present invention concerns the construction of ultrasonic energy receiving means (transducer) wherein by modifications made to the mechanical construction thereof, the receiving means is rendered suitable for particle purposes, for instance:

1. It is possible to construct a significantly smaller and more compact transducer which is no larger than the well known piezoelectric transducer test probe, yet has the advantage of exhibiting an extremely wide bandwidth since the light beam is free of inertia when compared with the heretofore known piezoelectric transducer probe.

2. Ultrasonic energy receivers in which the receiving surface can be selectively predetermined as to configuration and size; for instance, by means of selectively masking the receiving surface in a predetermined pattern, a focussed receiver is obtained. This possibility enables a receiver to be adapted for different purposes in contrast with the heretofore required changing of probes. For instance, it is necessary merely to interpose different light baffles in the light path instead of changing probes.

3. Receiving transducer probes which for the purposes of investigating the acoustic energy in the cross section of the acoustic beam are provided with a relatively large receiving surface adapted to be scanned in a raster by a point light source, hence obtaining excellent resolution.

The above features are achieved by providing an apparatus comprising a separate light source, a light conductor attached to a prism made of optical material, e.g. glass, as well as an interference means, preferably of optical prism material, having a higher refraction index than an intermediate medium disposed between said prism and interference means. The interference means is separated from the prism by a distance in the order of $10^{-7}$m to provide that either the prism or the interference means is excited for thickness vibration, particularly vibrations of the boundary surfaces, and to cause the reflected portion of the light beam as well as the beam portion transmitted into the interference means to be responsive to the frequency of the thickness change of the interposed medium, or expressed otherwise, to cause the light beam apparent at the prism and/or the interference means to be modulated by the frequency of the ultrasonic signal incident upon the transducer.

A commercially available incandescent lamp can be used as light source since the effects of the wavelength of the light, of the polarization and incident angle are not particularly critical if the limiting angle given by the total reflection is exceeded by a sufficient amount.

Details of the invention will be more clearly understood by reference to the following description when taken in conjunction with the accompanying drawings.

DETAILED DESCRIPTION

Figure 1:
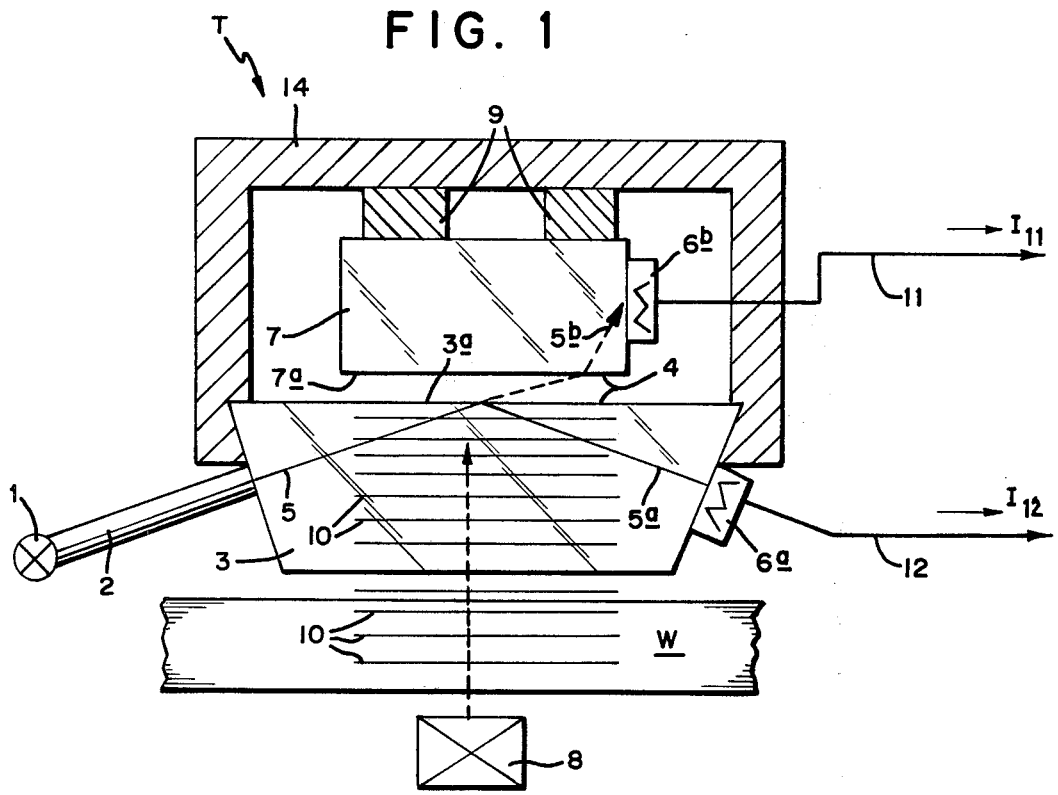
FIG. 1 is a side elevational side view, partly in section, of a typical embodiment of the present invention.

Referring now to the figures and FIG. 1 in particular showing the novel transducer means T, an external, separately cooled light source 1 produces a beam of light 5 which is conducted via a light conductor 2 into a prism 3 supported in an enclosure 14. The index of refraction of the prism must be greater than that of the abutting medium, preferably gas, which constitutes an intermediate layer 4 disposed between the prism 3 and an interference means 7, the latter being in the form of a refractive element, typically a glass plate. This arrangement produces at the surface, that is at the boundary layer between the prism surface 3a and the intermediate layer 4, total reflection, provided that the angle of incidence of the light beam is greater than the corresponding limiting angle. However, the reflection is subject to the described disturbance or interference by virtue of the close proximity of the interference means 7 to the prism 3. The reflected light beam 5a, reflected at the boundary surface, is transformed to an electrical signal via an opto-electrical transducer 6a, such as a photoelectric diode, coupled to the prism 3. Based on the above explanation, the following can be stated. At the interface between the prism 3 and the intermediate layer 4 the light in the intermediate layer is converted to a surface wave whose amplitude diminishes rapidly in a direction normal to the surface 3a of the prism 3 in the direction toward the optical interference means 7, which has a greater index of refraction than that of the intermediate layer 4. The interference is conditioned upon the presence of the interference means 7 within an effective distance which is less than one wavelength of light. Hence, the interference means 7 with its surface 7a, i.e. with its surface abutting the intermediate layer 4, interferes only with the surface wave. Resulting from this phenomenon, the light beam enters the interference means 7. The intensity ratio of the reflected light portion 5a to the transmitted light portion 5b is dependent upon the gap between the plane, gap abutting surfaces 3a and 7a, that is the thickness of the intermediate layer 4. The thickness of the intermediate layer in practice is selected to have a magnitude in the order of $10^{-7}$m. By suitably selecting the thickness of the layer 4 a predetermined operating point for the present method is attained. The thickness is adjusted in a static manner by the use of predetermined spacing members 9 disposed between the housing 14 and the rear surface of the interference means 7.

Figure 8:
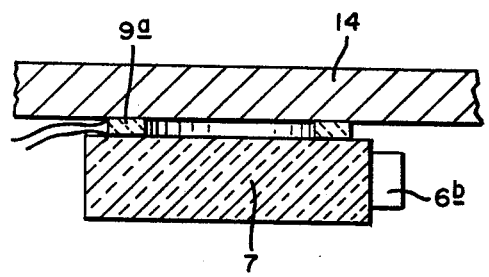
FIG. 8 is a sectional view showing a modification of the embodiment per FIG. 1.

Instead of the spacing members 9 it is possible also to interpose a piezoelectric spacer 9a FIG. 8 to provide for controlling with an electrical voltage applied to the conductors extending from the spacer electrodes the thickness of the intermediate layer. Alternatively, the piezoelectric spacer can be enerergized with an alternating voltage signal to cause the intermediate layer thickness to be modulated by means of the spacing member with a frequency which, preferably, is selected to be higher than that of the acoustic signal frequency. This modulation causes the electrical output signals from photoelectric transducers 6a and 6b to be a modulated high frequency signal which is more readily processed as is known in the art.

Figure 2:
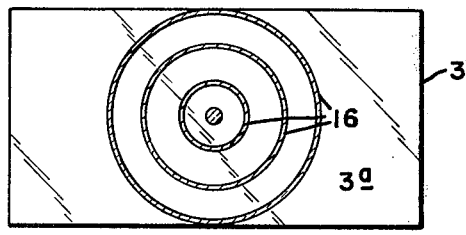
FIG. 2 is a plan view showing masking of the prism surface.

There is shown, moreover, a source of acoustic energy 8 from which ultrasonic waves 10, either reflected or transmitted energy, are transmitted through a workpiece W (using a suitable couplant between the workpiece and source 8, and the workpiece and prism 3 respectively) toward the prism 3, causing ultrasonic vibrations to be propagated through the prism with the result that there occurs a deflection, i.e. a shift of the end surface 3a in synchronism with the ultrasonic waves. Also, interference of the total reflection occurs in synchronism with the utrasonic waves. In this manner, both the reflected light beam 5a and the transmitted light beam 5b having passed through the interference means 7 are intensity modulated with the frequency of the ultrasonic wave source and, as applicable, with the motion of the periodically excited spacing member 9. Both beams are transformed to electrical signals by the opto-electrical transducers 6a and 6b and the signals are conducted via respective conductors 11 and 12 to a respective amplifier or similar circuit. Typically, the difference between the respective electrical currents, i.e. $I_{11} - I_{12}$, is formed and indicated or utilized otherwise. In a simplified embodiment, only one of the output signals is used. As seen in FIG. 2, the surface 3a of the prism can be masked in a specific pattern 16, such as a Fresnel zone pattern. In this manner, the surface is modified optically to derive a zoned plane which produces a focussed utrasonic receiver probe since only a portion of the surface 3a is effective for optical to electrical signal conversion.

Figure 3:
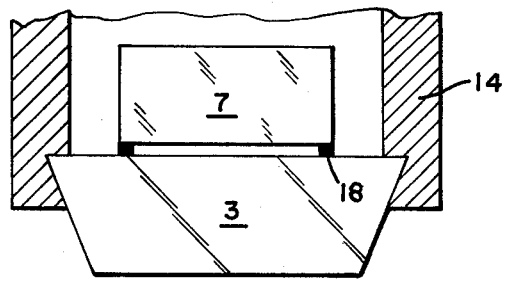
FIG. 3 shows an alternative construction for providing spacing between the prism and the interference means.

In order to provide accurate spacing between the prism 3 and the interference means 7, FIG. 3 shows a construction wherein an evaporated metal layer 18 is used between the gap abutting surfaces. Typically, the layer 18 is chromium 200 nanometer thick.

Figure 6:
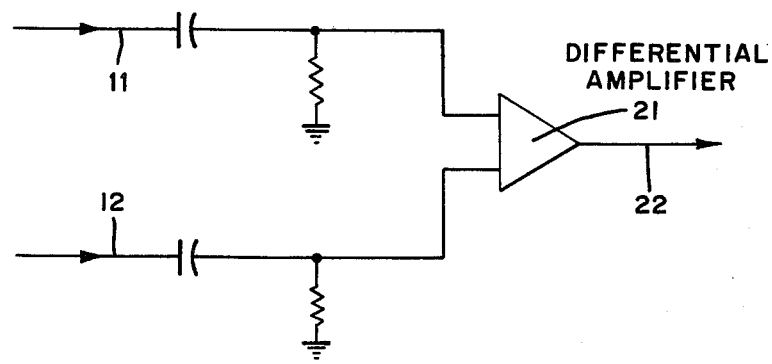
FIG. 6 is a schematic electrical diagram.

FIG. 6 shows an electrical circuit for improving the signal to noise ratio of the electrical output signals by connecting the conductors 11 and 12 to the input of a differential amplifier 21. The output from the differential amplifier, conductor 22, provides a greatly improved electrical signal which is responsive to the ultrasonic wave incident upon the transducer probe.

Figure 4:
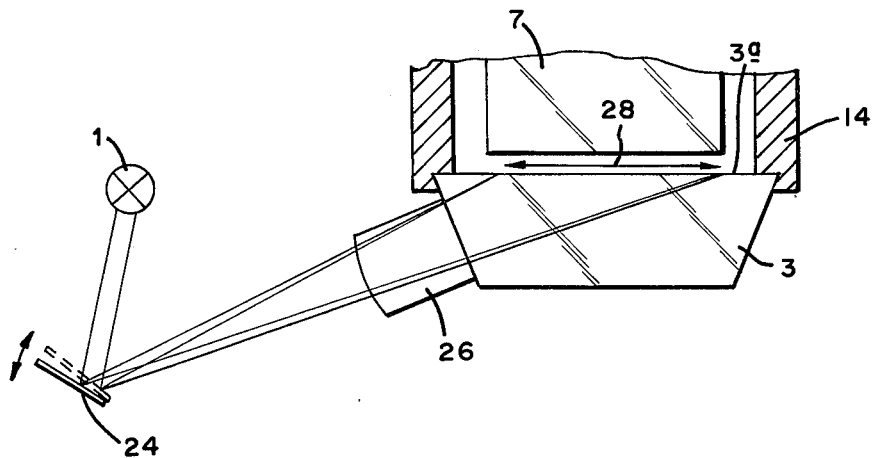
FIG. 4 is a schematic illustration for optically scanning the prism surface.

It is readily possible to utilize the light beam 5 for scanning the sound beam cross section to determine the distribution of sonic energy in the sound field. Scanning, referring to FIG. 4, can be accomplished by a rotating or oscillating mirror which reflects the light from the source of light 1. The light from the source 1 reflected at the surface of the mirror 24 is transmitted toward a planoconvex lens 26 which serves as a light conductor for causing the beam of light to enter the prism 3. As the mirror rotates about a small angle, the beam of light performs a line scan as indicated by arrow 28 along the surface 3a of the prism. The light spot produced at the surface 3a must be smaller than the smallest element of the sound beam cross section to be resolved. As stated heretofore, the angle of incidence of the light must be greater than the corresponding limiting angle.

Figure 5:
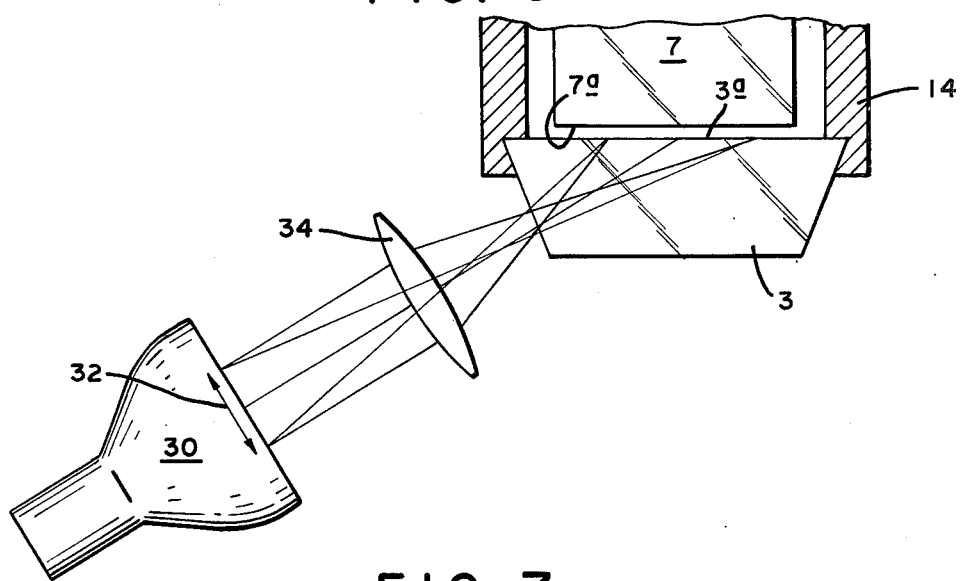
FIG. 5 is a schematic illustration showing another arrangement for optically scanning the prism surface.

FIG. 5 shows an alternative scanning arrangement. A flying spot scanner tube 30 is used to provide a linear oscillating scan in the direction of arrow 32. The light is projected via a suitable lens 34 or via a planoconvex light conductor 26 (FIG. 4) toward the prism 3. The line scan at the screen of the tube 30 is reproduced along the prism surface 3a, hence providing the same result as is achieved with the embodiment per FIG. 4.

Figure 7:
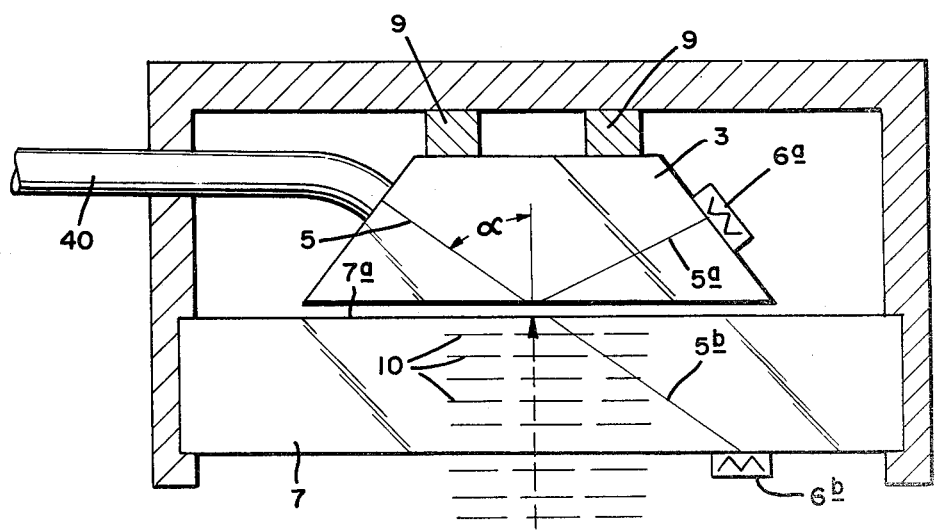
FIG. 7 is a side elevational view, partly in section, of an alternative embodiment of the invention shown in FIG. 1.

FIG. 7 depicts an alternative embodiment of the present invention wherein the ultrasonic energy is transmitted to the interference means and the light beam, as previously described, is coupled to the prism. With reference to FIG. 7, the beam of light is conducted via a light conductor 40 to the prism 3. Light reflected at the surface 3a is received by the photoelectric means 6a, beam 5a. Ultrasonic energy 10 is propagated toward the surface 7a. Except for the acoustic energy reaching the surface 7a instead of the surface 3a as seen in FIG. 1, the operation of the transducer is identical. The output from the photodiodes 6a and 6b will be responsive to the motion of the surface 7a, such motion being caused by the sonic wave energy 10. With reference to the embodiment per FIG. 7 it should be observed that the single $\alpha$ must be greater than the limiting angle wherein $$\sin\alpha_{limit} = 1/n,$$

n being the index of refraction of the prism and of the interference means material if the intermediate layer 4, for example air, has an index of refraction of unity.

While as shown in FIG. 1, the transducer means T is used as a receiver in the through transmission test mode, it will be apparent that the transducer probe can be used also as a receiver probe in the pulse reflection test mode.

What is claimed is:

1. Transducer means for receiving ultrasonic energy and transforming such energy to an electrical signal comprising:
    an optical prism;
    means supporting said prism;
    an optical interference means disposed opposite said prism;
    means spacing said prism from said interference means to cause a gap with the respective oppositely disposed gap abutting surfaces separated by a distance in the order of $10^{-7}$ meter;
    a layer of an intermediate medium having a lower index of refraction than that of said interference means filling said gap between said prism and said interference means;
    a source of light spaced from said prism and coupled to said prism by light conducting means for causing a beam of light to enter said prism and be incident upon the gap abutting surface of said prism, causing a portion of said light beam to be reflected at said gap abutting surface of said prism and causing another portion of said beam to be transmitted through said intermediate medium into said interference means, and
    photoelectric means coupled for sensing the variations of the light intensity of at least one beam portion responsive to ultrasonic wave energy transmitted to one of said abutting surfaces causing a periodic change in the thickness of said layer.

2. Transducer means as set forth in claim 1, and ultrasonic wave energy means disposed to cause such energy to be transmitted through said interference means to said gap abutting surface of said prism.

3. Transducer means as set forth in claim 1, and ultrasonic wave energy means disposed to cause the energy to be transmitted through said interferences means to said gap abutting surface of said interference means.

4. Transducer means as set forth in claim 1, said means spacing comprising a metal film disposed between said prism and said interference means.

5. Transducer means as set forth in claim 1, said means spacing comprising piezoelectric means adapted to be energized with an electrical potential.

6. Transducer means as set forth in claim 1, said means spacing comprising piezoelectric means, and means coupled for energizing said piezoelectric means with an alternating current potential.

7. Transducer means as set forth in claim 6, said alternating current potential having a frequency which is higher than that of said ultrasonic wave energy.

8. Transducer means as set forth in claim 1, said photoelectric means being coupled to said prism.

9. Transducer means as set forth in claim 1, said photoelectric means being coupled to said interference means.

10. Transducer means as set forth in claim 1, said photoelectric means comprising a first photoelectric means coupled to said prism and a second photoelectric means coupled to said interference means.

11. Transducer means as set forth in claim 10 and including a differential amplifier coupled for receiving the output from said first and said second photoelectric means.

12. Transducer means as set forth in claim 1, and masking means applied to said gap abutting surface of said prism to produce a predetermined optical pattern thereat.

13. Transducer means as set forth in claim 1, said intermediate medium being gas.

14. Transducer means as set forth in claim 13, said gas being air.

15. Transducer means as set forth in claim 1, said source of light comprising a source of visible light.

16. Transducer means for receiving acoustic wave energy and transforming said energy to an electrical signal comprising:
   a housing;
   an optical prism supported by said housing;
   an optical interference means supported by said housing and disposed opposite said prism;
   means spacing said prism and said interference means from one another to cause the respective oppositely disposed surfaces to be distanced by a gap in the order of $10^{-7}$ meter;
   a layer of gas filling said gap;
   a source of visible light spaced from said prism and coupled to said prism by light conducting means for causing a beam of light to enter said prism and be incident upon the gap abutting surface of said prism, causing a portion of said light beam to be reflected thereat and causing another portion of said light beam to be transmitted through said layer of gas and enter said interference means, and
   photoelectric means coupled to at least said prism or said interference means for sensing variations of the respective light beam portion caused by changes in said gap distance responsive to acoustic energy transmitted to one of said surfaces abutting said gap.

17. Transducer means as set forth in claim 16, said photoelectric means being coupled to both said prism and said interference means.

18. Transducer means as set forth in claim 16, and means coupled to said photoelectric means for processing the signals from said photoelectric means.

19. Transducer means as set forth in claim 16, and oppositely disposed surfaces being plane surfaces.

20. Transducer means as set forth in claim 16, the angle of incidence of the light upon said gap abutting surface of said prism being greater than the corresponding limiting angle.

21. Transducer means for receiving ultrasonic energy and transforming such energy to an electrical signal comprising:
   an optical prism;
   an optical interference means disposed opposite said prism;
   means spacing said prism and said interference means from one another to cause a gap with the respective oppositely disposed gap abutting surfaces separated by a distance in the order to $10^{-7}$ meter;
   a layer of an intermediate medium having a lower index of refraction than that of said interference means filling said gap between said prism and said interference means; a source of light disposed for causing a beam of light to enter said prism and be incident as a spot upon the gap abutting surface of said prism, causing one portion of said light beam to be reflected at said gap abutting surface of said prism and causing another portion of said beam to be transmitted through said intermediate medium into said interference means;
   means for causing said spot to scan the gap abutting surface of said prism and,
   photoelectric means coupled for sensing the variations of the light intensity of at least one of said portions of said light beam responsive to utrasonic wave energy transmitted to one of said abutting surfaces causing a periodic change in the thickness of said layer.

22. Transducer means as set forth in claim 21, said means for causing said spot to scan said surface including a movable mirror.

23. Transducer means as set forth in claim 21, said source of light comprising a flying spot scanner.

* * * * *

UNITED STATES PATENT AND TRADEMARK OFFICE
CERTIFICATE OF CORRECTION

PATENT NO. : 4,132,117
DATED : January 2, 1979
INVENTOR(S) : Erik Primbsch

It is certified that error appears in the above-identified patent and that said Letters Patent are hereby corrected as shown below:

Column 1, line 11, cancel "electric" and substitute -- electrical --.

Column 1, line 33, cancel "electricl" and substitute -- electrical --.

Column 2, line 10, cancel "resolutions" and substitute -- resolution --.

Column 2, line 27, cancel "indexed" and substitute -- indexes --.

Column 2, line 41, cancel "feeding" and substitute -- facing --.

Column 6, line 10, cancel "single" and substitute -- angle --.

Claim 2, line 3, cancel "interference" and substitute -- prism --.

Claim 3, line 2, cancel "the" and substitute -- such --.

Claim 3, line 3, cancel "interferences" and substitute -- interference --.

Claim 19, line 1, cancel "and" and substitute -- said --.

Claim 21, line 26, cancel "utrasonic" and substitute -- ultrasonic --.

Signed and Sealed this

Twelfth Day of June 1979

[SEAL]

Attest:

RUTH C. MASON
Attesting Officer

DONALD W. BANNER
Commissioner of Patents and Trademarks